(12) United States Patent
Li et al.

(10) Patent No.: US 9,328,136 B2
(45) Date of Patent: May 3, 2016

(54) METHOD OF PROTEIN PURIFICATION

(71) Applicant: NATIONAL CHIAO TUNG UNIVERSITY, Hsinchu (TW)

(72) Inventors: Yaw-Kuen Li, Hsinchu (TW); Yue-Jin Wu, Yunlin County (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 13/753,496

(22) Filed: Jan. 29, 2013

(65) Prior Publication Data

US 2014/0031531 A1  Jan. 30, 2014

(30) Foreign Application Priority Data

Jul. 27, 2012  (TW) .............................. 101127230 A (51) Int. Cl.
*C07K 17/06* (2006.01)
*C07K 17/14* (2006.01)
*C07K 1/14* (2006.01)
*C07K 1/22* (2006.01)

(52) U.S. Cl.
CPC ... *C07K 1/14* (2013.01); *C07K 1/22* (2013.01); *C07K 2319/00* (2013.01)

(58) Field of Classification Search
CPC ..... C07K 17/06; C07K 17/14; C07K 2319/21
USPC ........................................................ 435/200
See application file for complete search history.

(56) References Cited

U.S. PATENT DOCUMENTS

| 6,933,362 B1 | 8/2005 | Belfort et al. |
| 2003/0114648 A1 | 6/2003 | Haj-Ahmad |
| 2008/0108123 A1 | 5/2008 | Imamura et al. |
| 2010/0317083 A1* | 12/2010 | Allhorn et al. ................ 435/200 |
| 2013/0227718 A1* | 8/2013 | Matsuda et al. ................ 800/13 |

FOREIGN PATENT DOCUMENTS

TW  201122110 A1  7/2011

OTHER PUBLICATIONS

Purification of recombinant enhanced green fluorescent protein expressed in *Escherichia coli* with new immobilized metal ion affinity magnetic absorbents. Chiang CL, Chen CY, Chang LW. J Chromatogr B Analyt Technol Biomed Life Sci. Mar. 15, 2008;864(1-2):116-22. Epub Feb. 20, 2008.

A novel self-cleaving phasin tag for purification of recombinant proteins based on hydrophobic polyhydroxyalkanoate nanoparticles. Wang Z, Wu H, Chen J, Zhang J, Yao Y, Chen GQ,. Lab Chip. Nov. 2008;8(11):1957-62. Epub Aug. 29, 2008.

Nejadmoghaddam et al., "Profiling and quantitative evaluation of three Nickel-Coated magnetic matrices for purification of recombinant proteins: lelpful hints for the optimized nanomagnetisable matrix preparation," Journal of Nanobiotechnology 2011, 9:31.

* cited by examiner

*Primary Examiner* — Maryam Monshipouri
(74) *Attorney, Agent, or Firm* — CKC & Partners Co., Ltd.

(57) ABSTRACT

A method for producing a target protein is provided, which includes steps described below. A crude extract including a fusion protein is provided. The fusion protein includes a tag, a target protein and a linker inserted between the tag and the target protein. The fusion protein and magnetic particles are then bound to form a magnetic particle-binding fusion protein. Finally, the linker of the magnetic particle-binding fusion protein undergoes autocleavage by using a cleavage buffer solution to release the target protein. A one-pot process for producing a purified target protein is also provided.

18 Claims, 8 Drawing Sheets

METHOD OF PROTEIN PURIFICATION

RELATED APPLICATIONS

This application claims priority to Taiwan Application Serial Number 101127230, filed Jul. 27, 2012, which is herein incorporated by reference.

BACKGROUND

1. Technical Field

The present disclosure relates to a method for producing a target protein and a one-pot process for producing a purified target protein.

2. Description of Related Art

Using specific functional groups-containing gel to perform affinity binding with another functional group is the best approach of purifying a protein. However, a protein column chromatography, as the commonly used process of purifying a protein, still has many shortcomings to be overcome.

Generally, the protein column chromatography includes the steps of binding, washing and elution in sequence. In the step of washing, imdazole buffer solutions with different pH values are used to rinse the column to wash away impurities, such that this step is time consuming. Also, in the step of elution, protease is used to break the linker to obtain the target protein. If the specificity of the selected protease to the linker is low, it is difficult to obtain the highly pure target protein. Moreover, the used column in the process cannot be reused. Given the above, the process speed and effect of purification for the protein column chromatography need to be improved.

As a result, there is a need for a cost-effective method for the mass production of the high purity of the target protein.

SUMMARY

One aspect of the present disclosure provides a method for producing a target protein, which includes the steps below. A crude extract including a fusion protein is provided. The fusion protein includes a tag, a target protein and a linker inserted between the tag and the target protein. The magnetic particles and the fusion protein of the crude extract are then bound to form a magnetic particle-binding fusion protein. Finally, the linker of the magnetic particle-binding fusion protein undergoes autocleavage, which is enabled by using a cleavage buffer solution to release the target protein.

Another aspect of the present disclosure provides a one-pot process for producing a purified target protein, which includes the steps below. A crude extract including a fusion protein is provided. The fusion protein includes a tag, a target protein and a linker inserted between the tag and the target protein. The crude extract, a solution and magnetic particles are mixed to form a magnetic particle-binding fusion protein. A cleavage buffer solution and the magnetic particle-binding fusion protein are mixed to let the linker of the magnetic particle-binding fusion protein undergo autocleavage to thereby release the target protein and the magnetic residues. The target protein is then removed.

Another aspect of the present disclosure provides a fusion protein applied to the one-pot process mentioned above. The fusion protein includes a tag, a linker and a target protein. The tag is a plurality of histidine. The linker is connected to the tag, and includes at least one primary amino acid sequence selected from the group consisting of $(EA_{m1}K)_{n1}$, $(EA_{m2}R)_{n2}$, $(EG_{m3}K)_{n3}$, $(EG_{m4}R)_{n4}$, $(DA_{m5}K)_{n5}$, $(DA_{m6}R)_{n6}$, $(DG_{m7}K)_{n7}$, $(DG_{m8}R)_{n8}$, $(KA_{m9}E)_{n9}$, $E(N_{p1})K$, $E(N_{p2})R$, $D(N_{p3})K$, $D(N_{p4})R$ and a combination thereof, in which m1, m2, m3, m4, m5, m6, m7, m8 and m9 are respectively equal or greater than 2. n1, n2, n3, n4, n5, n6, 7, n8 and n9 are respectively equal or greater than 2. N is glycine (G), valine (V), leucine (L), isoleucine (I), serine (S), threonine (T) or cysteine (C), p1, p2, p3 and p4 are respectively equal or greater than 2. The target protein is connected to the linker.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The disclosure may be more fully understood by reading the following detailed description of the embodiment, with reference made to the accompanying drawings as follows.

DETAILED DESCRIPTION

The present disclosure is described by the following specific embodiments. Those with ordinary skill in the arts can readily understand the other advantages and functions of the present invention after reading the disclosure of this specification. The present disclosure can also be implemented with different embodiments. Various details described in this specification can be modified based on different viewpoints and applications without departing from the scope of the present disclosure.

Reference will now be made in detail to the embodiments of the present disclosure, examples of which are illustrated in the accompanying drawings. Wherever possible, the same reference numbers are used in the drawings and the description to refer to the same or like parts.

Figure 1:
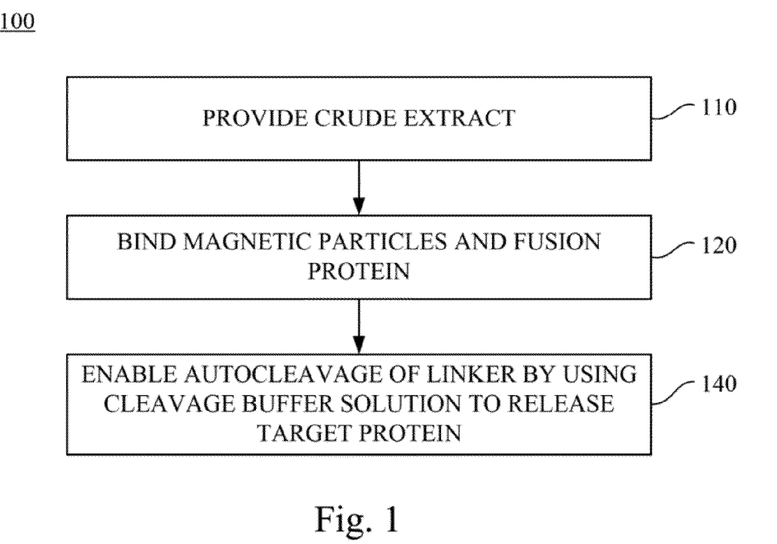
FIG. 1 is a flow chart of a method for producing a target protein according to one embodiment of the present disclosure.

One aspect of the present disclosure provides a method for producing a target protein, as shown in FIG. 1. FIG. 1 shows a flow chart of the steps in a method 100.

In step 110, a crude extract including a fusion protein is provided. The fusion protein includes a tag, a target protein and a linker inserted between the tag and the target protein. Specifically, the term "fusion protein" refers to a recombinant protein expressed by a vector, and it includes a tag, a linker and a to target protein from N-terminal to C-terminal. Construction of DNA expression vectors is well known in the art, and thus is omitted herein.

The tag should bind with magnetic particles. The type of the tag is not limited herein. For instance, the tag can be His-tag, such as more than or equal to 6 histidines. Since the His-tag has high affinity with metal ions (e.g., nickel or cobalt ions), the metal ions on the surfaces of the magnetic particles binds the His-tag of the fusion protein to form a magnetic particle-binding fusion protein by mixing the magnetic particles and the crude extract.

The term "target protein" herein refers to an interested molecule. Suitable target protein includes, but is not limited to, enzymes such as chitosanase, chitinase, laminaripentaose-producing-β-1,3-glucanase (LPHase), hydrolase, transferase, lyase, isomerase, methylase, endonuclease or ligase; storage proteins such as ovalbumin; transport proteins such as hemoglobin; structural proteins such as actin, myosin, collagen, elastin, α-keratin, glycoprotein and fibrous protein; immunological proteins such as antigens or antigenic determinants that can be used to prepare vaccines; blood proteins such as thrombin and fibrinogen; binding proteins such as antibodies or immunoglobulins that bind and neutralize antigens; hormones such as growth factors, somatostatin, prolactin, estrogen, progesterone, insulin, interleukins, colony stimulating factor and interferon; and synthetic proteins and peptides. For examples, the target protein may be green fluorescent protein (GFP), m-Cherry protein, maltose binding protein or other hydrophilic proteins, but not limited thereto.

The linker includes at least one primary amino acid sequence. In one embodiment, the primary amino acid sequence is selected from the group consisting of (EA$_{m1}$K)$_{n1}$, (EA$_{m2}$R)$_{n2}$, (EG$_{m3}$K)$_{n3}$, (EG$_{m4}$R)$_{n4}$, (DA$_{m5}$K)$_{n5}$, (DA$_{m6}$R)$_{n6}$, (DG$_{m7}$K)$_{n7}$, (DG$_{m7}$R)$_{n8}$, (KA$_{m9}$E)$_{n9}$, E(N$_{p1}$)K, E(N$_{p2}$)R, D(N$_{p3}$)K, D(N$_{p4}$)R and a combination thereof, in which m1, m2, m3, m4, m5, m6, m7, m8 and m9 are respectively equal or greater than 2. n1, n2, n3, n4, n5, n6, n7, n8 and n9 are respectively equal or greater than 2. N is glycine (G), valine (V), leucine (L), isoleucine (I), serine (S), threonine (T) or cysteine (C). p1, p2, p3 and p4 are respectively equal or greater than 2. The linker can be (EAAAK)$_3$, (EAAAR)$_3$, (EGGGK)$_3$, (EGGGR)$_3$, (DAAAR)$_3$, (DAAAK)$_3$, (DGGGR)$_3$, (DGGGK)$_3$, (EAAAAK)$_3$, (KAAAE)$_4$, (KAAAE)$_2$(EAAAK)$_2$ or (EAAAK)$_2$(KAAAE)$_2$ In one embodiment, the linker further includes (G$_{x1}$S)$_{y1}$, in which G connects to the tag. S connects to the primary amino acid sequence. x1 is equal or greater than 3. y1 is equal or greater than 2. The linker can be (GGGGS)$_3$(EAAAK)$_2$.

In one embodiment, the linker further includes (G$_{x2}$S)$_{y2}$ inserted between two identical or different primary amino acid sequences, in which x2 is equal or greater than 3, and y2 is equal or greater than 2. The linker can be (KAAAE)$_2$(GGGS)$_2$(EAAAK)$_2$.

In one embodiment, the linker further includes (SG$_{x3}$)$_{y3}$H$_z$(G$_{x4}$S)$_{y4}$ inserted between two identical or different primary amino acid sequences, in which x3 and x4 are respectively equal or greater than 3, y3 and y4 are respectively equal or greater than 2. z is more than or equal to 6. The linker can be (KAAAE)$_2$(SGGG)$_2$HHHHHH(GGGS)$_2$(EAAAK)$_2$.

The crude extract can be prepared by employing any technique in the art. For instance, the cell membranes of host cells are broken by mechanical or chemical treatment, and the crude extract is then collected by centrifugation. The crude extract contains not only "fusion protein containing the target protein" but also impurities. The impurities may be other products formed during expression of vectors. For example, the impurities may contain "fusion protein containing non-target protein." Specifically, the "fusion protein containing non-target protein" can be a fusion protein including the tag, the linker and the non-target protein from N-terminal to C-terminal. Therefore, the impurities should be totally removed during the purification process, and the linker then undergoes autocleavage to obtain the highly pure target protein. How to achieve the objective would be described in detail below.

In step 120, the magnetic particles and the fusion protein of the crude extract are bound to form a magnetic particle-binding fusion protein. Since the surface of the magnetic particle has some functional groups able to bind with the tag, so as to form the magnetic particle-binding fusion protein. However, in step 120, there are still some fusion proteins not binding with the magnetic particles.

The magnetic particles may be magnetic nanoparticles. Compared to the conventional column, the magnetic particles have the advantages of reusable, cheap and able to simplify the process. In one embodiment, the surface of the magnetic particle has at least one group selected from the group consisting of a nickel ion, a cobalt ion, 1,6-diaminohexane, 1-octylamine, oleylamine, tri-n-octylphosphine oxide, tri-n-octylphosphine and a combination thereof.

In one embodiment, the surface of the magnetic particle can be modified with nitrilotriacetic acid (NTA) groups, and then modified with nickel ions ($Ni^{2+}$) or cobalt ions ($Co^{2+}$). NTA groups can form coordinate bond with nickel (or cobalt) ions, and the metal ions can form coordinate bond with His-Tags. Before reusing magnetic particles, nickel (or cobalt) ions and protein residues are removed by using ethylene diamine tetraacetic acid (EDTA). Subsequently, EDTA is removed, and NTA groups and nickel (or cobalt) ions are then modified on the surfaces of the magnetic particles in sequence.

In another embodiment, magnetic particles applied in protein purification process are synthesized. For one example, 25 g coprecipitation agent is added in 10 g nickel chloride ($NiCl_2$)/200 ml glycol. The coprecipitation agent can be sodium hydroxide (NaOH), sodium bicarbonate ($NaHCO_3$), sodium acetate ($CH_3COONa$) or a mixture thereof. Next, $NiCl_2$ and the coprecipitation agent are dissolved at 80° C., and then heated to 200° C. for 12 hours. For another example, various ratios of iron chloride ($FeCl_2$) and $NiCl_2$ are employed to synthesize alloy magnetic nanoparticles. For examples, the ratios of the $FeCl_2$ and $NiCl_2$ respectively are 1:1, 1:2, 1:3, 1:5, 1:7, 2:1, 3:1 or 4:1. For another example, a variety of reagents are added to modify ligands with different characteristics on the surfaces of the magnetic nanoparticles. The ligands can be hydrophilic groups, such as 1,6-diaminohexane; the ligands can be hydrophobic groups, such as 1-octylamine, oleylamine, tri-n-octylphosphine oxide or tri-n-octylphosphine.

In one embodiment, step 120 includes mixing the fusion protein and the magnetic particles in a solution. The composition of the solution is not limited herein. For one example, the solution is 10 mM TRIS buffer (pH=9).

In one embodiment, after step 120, the method further includes removing the solution by fixing the magnetic particle-binding fusion protein. Most of impurities are removed during removing the solution. The impurities may contain the fusion protein that does not bind with the magnetic particles, and other substances.

In one embodiment, after removing the solution and before step 130, the method further includes washing the magnetic particles by a wash buffer solution. Step 130 is employed to flush out impurities to only leave the magnetic particle-binding fusion protein having the target protein as much as possible. In one embodiment, the wash buffer solution has a pH value more than 7. The composition of the wash buffer solution is not limited herein. For one example, TRIS buffer with pH=9 is used as the wash buffer solution to flush the magnetic particles for many times. Given above, the step of removing the solution and the step of washing the magnetic particles can be carried out to remove impurities.

In step 130, the linker of the magnetic particle-binding fusion protein undergoes autocleavage by using a cleavage buffer solution to thereby release the target protein. In one embodiment, the linker undergoes autocleavage in buffer solution with pH=6–9. A suitable pH range of the cleavage buffer solution is related to the type of the linker. The composition of the cleavage buffer solution is not limited herein. For instance, the cleavage buffer solution may be TRIS buffer or phosphate buffer.

In one embodiment, the steps of the method are a one-pot process. The term "one-pot process" refers to the step of mixing the crude extract and the magnetic particles till the step of removing the target protein (i.e., all the purification process steps) are carried out in one container. Therefore, the one-pot process of the embodiments is convenient and fast, such that it can be applied in a large-scale protein purification process.

Figure 2:
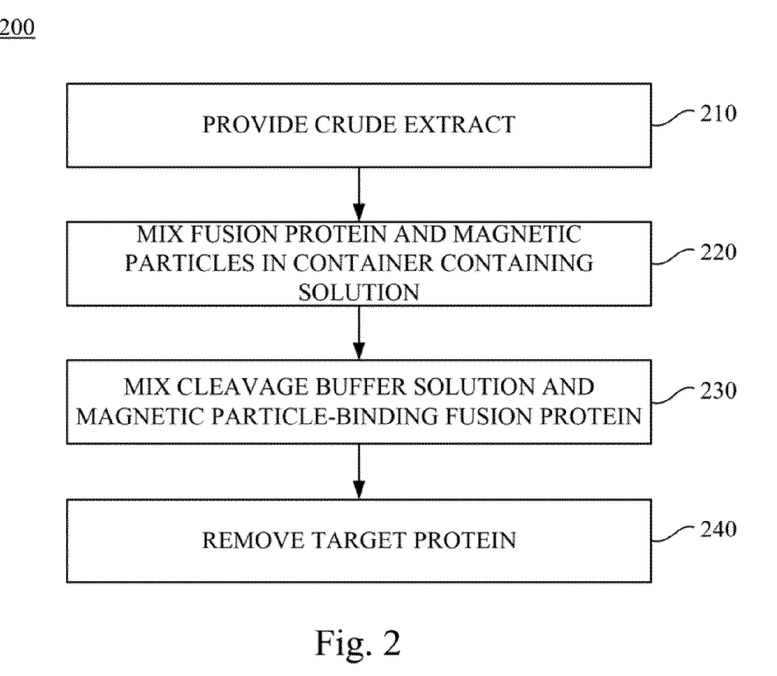
FIG. 2 is a flow chart of a one-pot process for producing a purified target protein according to one embodiment of the present disclosure.
Figure 3:
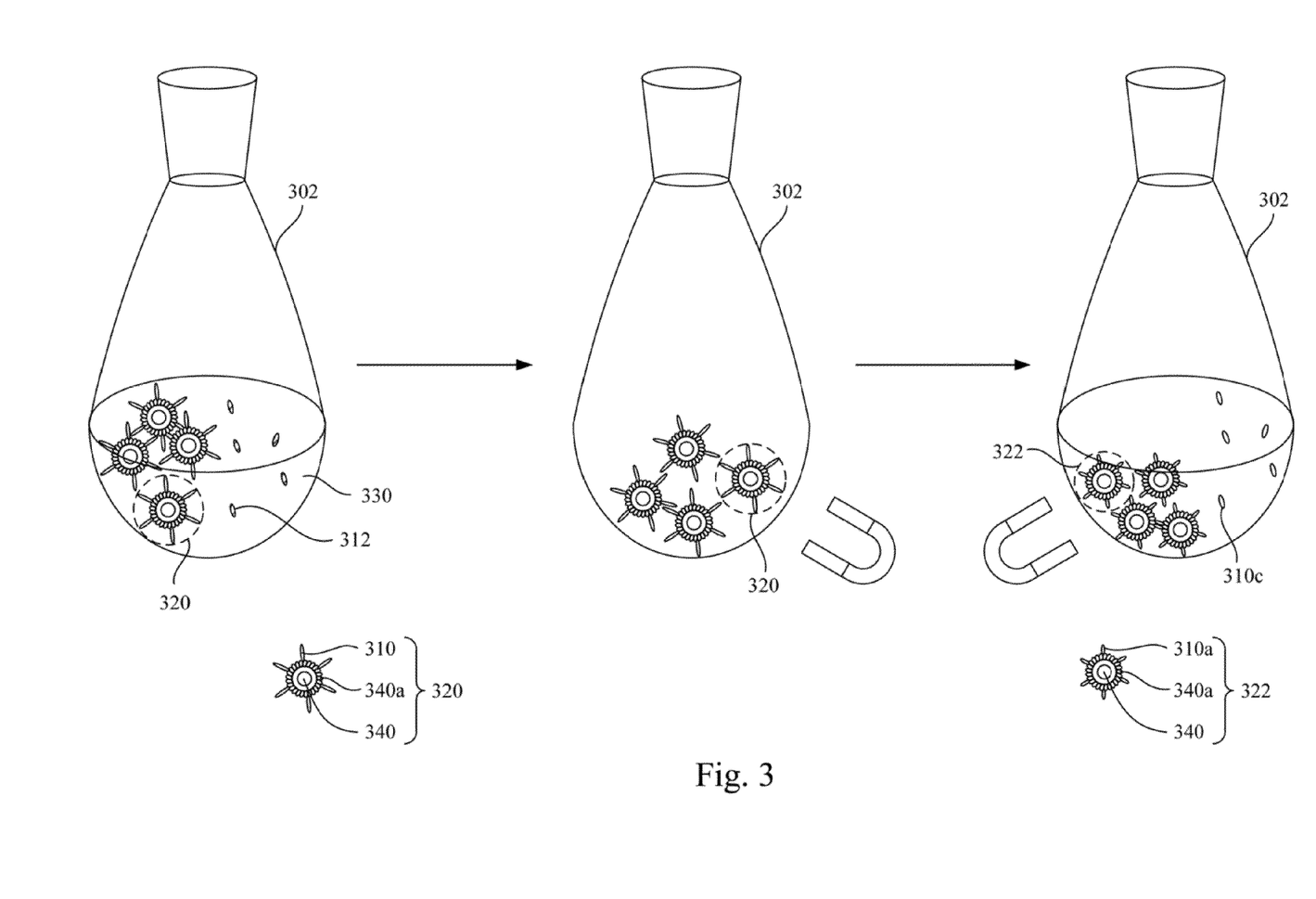
FIG. 3 is a schematic diagram of a device of protein purification according to one embodiment of the present disclosure.

Please refer to FIG. 2 and FIG. 3, another aspect of the present disclosure provides a one-pot process for producing a purified target protein. FIG. 2 is a flow chart of a one-pot process 200. FIG. 3 is a schematic diagram of a device of protein purification according to one embodiment of the present disclosure.

In step 210, a crude extract including a fusion protein 310 is provided. The fusion protein 310 includes a tag, a target protein 310c and a linker inserted between the tag and the target protein 310. The embodiments of step 210 can be the same as step 110.

In step 220, the crude extract containing the fusion protein 310 and impurities 312, a solution 320 and magnetic particles 340 are mixed in a container 302 to form a magnetic particle-binding fusion protein 320, as shown in FIG. 1. The functional groups 340a on the surfaces of the magnetic particles 340 binds with the tag. The embodiments of step 220 can be the same as step 120.

In one embodiment, the process further includes removing the solution 330 by fixing the magnetic particle-binding fusion protein 320 after step 220 and before 230, as shown in FIG. 2. For one example, a magnet is used to attract the magnetic particle-binding fusion protein 320 and the solution 330 is removed. However, there may still be a portion of impurities 312 jammed between the magnetic particle-binding fusion protein 320.

Hence, in one embodiment, the process further includes washing the magnetic particles 340 by using a wash buffer solution after the step of removing the solution 330 and before step 230. The washing step is employed to flush out remaining impurities 312 to only retain the magnetic particle-binding fusion protein 320 containing the target protein 310c. In one embodiment, the wash buffer solution has a pH value higher than 7. As mentioned above, the step of removing the solution 330 and the step of washing the magnetic particles 340 can be carried out to remove impurities 312. Preferably, the step of removing the solution 330 and the step of washing the magnetic particles 340 are performed in sequence.

In step 230, a cleavage buffer solution 350 and the magnetic particle-binding fusion protein 320 are mixed to enable the linker of the magnetic particle-binding fusion protein to undergo autocleavage, and thereby release the target protein 310c and the magnetic residues 322, as shown in FIG. 3. The magnetic residues may include the magnetic particles 340 and residues 310a. In one embodiment, the cleavage buffer solution 350 has a pH value equal or greater than 6. The embodiments of step 230 can be the same as step 130.

In one embodiment, the residues 310a is the tag.

In step 240, the target protein 310c is removed by fixing the magnetic residues 322. In one embodiment, a magnet is used to attract the magnetic residues 322. Consequently, supernatant fluid formed by step 240 is the solution containing highly pure target protein 310c.

The following examples serve to illustrate certain embodiments and aspects of the present disclosure and are not to be considered as limiting the scope thereof.

EXAMPLES

Example 1

Obtaining GFP from (his)$_6$-(EAAAK)$_3$-GFP

First, a crude extract containing (His)$_6$-(EAAAK)$_3$-GFP, 10 mM phosphate buffer solution (pH=7) and magnetic particles are mixed in a flask to let the tag (i.e., (His)$_6$) indeed bind the magnetic particle. The magnetic particles are produced from GE Healthcare Company. It is noted that (EAAAK)$_3$ refers to SEQ ID No:10.

Subsequently, the magnetic particles are attracted by a magnet and the solution is removed. In this step, the substances that do not bind with the magnetic particles are removed.

Next, the magnetic particles are flushed by a buffer solution (pH=9) for 3 times, and then flushed by another buffer solution (pH=7) for one time to indeed remove residual impurities.

Finally, the magnetic particles are dipped in a buffer solution (pH=7) for 48 hours at ambient temperature to let the linker undergo autocleavage to thereby release the target protein.

Figure 4:
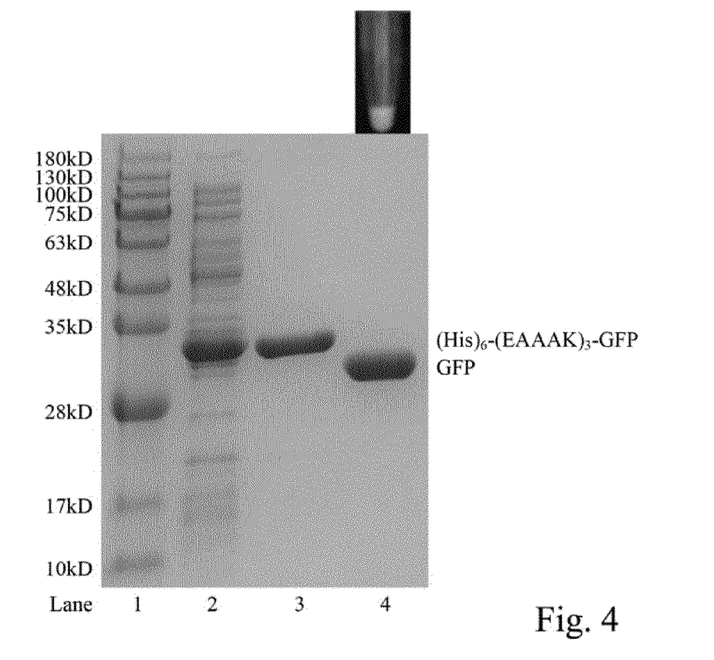
FIG. 4 is the SOS-PAGE analyses during purifying $(His)_6$-$(EAAAK)_3$-GFP. Lane 1: marker; Lane 2: crude extract; Lane 3: magnetic particle-binding fusion protein; Lane 4: green fluorescent protein (GFP)

As shown in FIG. 4, the molecular weight of the magnetic particle-binding fusion protein (Lane 3) slightly different from the GFP (Lane 4) indicates that the linker already undergoes cleavage to release the target protein into the solution. Given above, the one-pot process is a workable protein purification process to obtain the highly pure target protein.

Example 2

Obtaining m-Cherry Protein from (His)-GFP-(EAAAK)$_2$-m-Cherry

The steps of Example 2 are the same as the steps of Example 1, and the only difference is that the crude extract of Example 2 contains (His)$_8$-GFP-(EAAAK)$_2$-m-Cherry. It is noted that (EAAAK)$_2$ refers to SEQ ID No:11.

Figure 5:
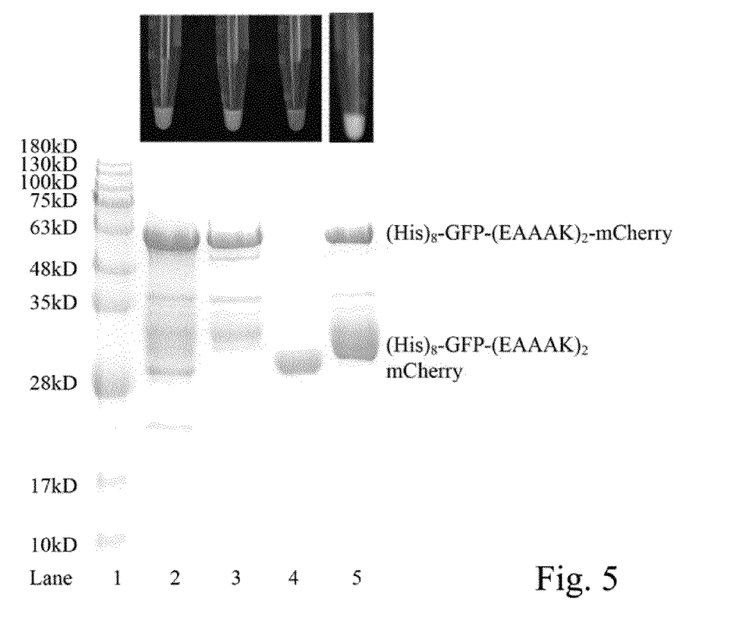
FIG. 5 is the SDS-PAGE analyses during purifying $(His)_8$-GFP-$(EAAAK)_2$-m-Cherry. Lane 1: marker; Lane 2: crude extract; Lane 3: magnetic particle-binding fusion protein; Lane 4: m-Cherry protein; Lane 5: a substances which still binds with magnetic particles after mixing the cleavage buffer solution and the magnetic particle-binding fusion protein.

As shown in FIG. 5, the magnetic particle-binding fusion protein (Lane 3) has various molecular weights and shows yellow color under ultraviolet light. It is indicates that the magnetic particle-binding fusion protein still contains other substances with different molecular weights.

After mixing a cleavage buffer solution, the linker undergoes autocleavage to obtain highly pure m-Cherry protein (Lane 4) and the substances that still binds with the magnetic particles (Lane 5). Two substances respectively show red color and green color under ultraviolet light. As shown in Lane 5 of FIG. 5, the substances which still binds with the magnetic particles may includes a portion of (His)$_8$-GFP-(EAAAK)$_2$-m-Cherry and (His)$_8$-GFP-(EAAAK)$_2$.

Example 3

Autocleavage of Linker of CBP21(KAAAE)$_2$(EAAAK)$_2$-AF-(His)$_6$

Purified CBP21-(KAAAE)$_2$(EAAAK)$_2$-AF-(His)$_6$ and 10 mM phosphate buffer solution (pH=7) are mixed, and then the linker undergoes autocleavage. It is noted that (KAAAE)$_2$(EAAAK)$_2$ refers to SEQ ID No:12.

Figure 6:
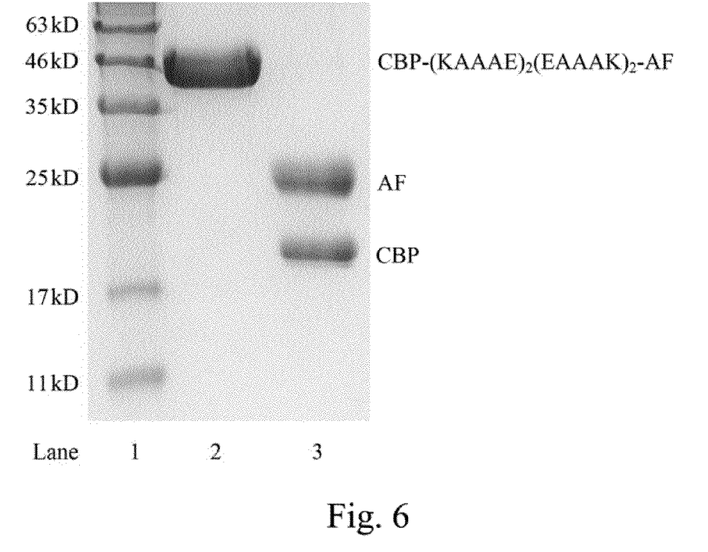
FIG. 6 is the SDS-PAGE analyses of autocleavage of linker of CBP21-$(KAAAE)_2(EAAAK)_2$-AF-$(His)_6$. Lane 1: marker; Lane 2: CBP21-$(KAAAE)_2(EAAAK)_2$-AF-$(His)_6$; Lane 3: AF protein and CBP.

As shown in Lane 2 (purified CBP21-(KAAAE)$_2$(EAAAK)$_2$-AF-(His)$_6$) and Lane 3 (AF protein and CBP) of FIG. 6, the linker undergoes autocleavage to obtain AF protein and CBP. Therefore, in the embodiment of the present disclosure, (KAAAE)$_2$(EAAAK)$_2$ is an effective linker.

Example 4

Autocleavage of Linker of CBP21-(KAAAE)$_2$(GGGS)$_2$(EAAAK)$_2$-AF-(His)$_6$

The steps of Example 4 are the same as the steps of Example 3, and the only difference is that CBP21-(KAAAE)$_2$(GGGS)$_2$(EAAAK)$_2$-AF-(His)$_6$ is used. It is noted that (KAAAE)$_2$(GGGS)$_2$(EAAAK)$_2$ refers to SEQ ID No:13.

Figure 7:
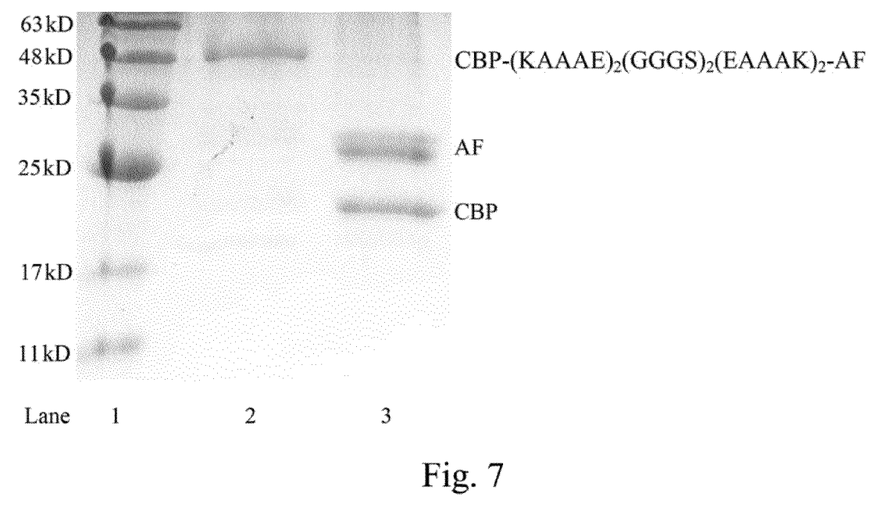
FIG. 7 is the SDS-PAGE analyses of autocleavage of linker of CBP21-$(KAAAE)_2(GGGS)_2(EAAAK)$-AF-$(His)_6$. Lane 1: marker; Lane 2: CBP21-$(KAAAE)_2(GGGS)_2(EAAAK)$-AF-$(His)_6$; Lane 3: AF protein and CBP.

As shown in Lane 2 (CBP21-(KAAAE)$_2$(GGGS)$_2$(EAAAK)$_2$-AF-(His)$_6$) and Lane 3 (AF protein and CBP) of FIG. 7, the linker undergoes autocleavage to obtain AF protein and CBP. Therefore, in the embodiment of the present disclosure, (KAAAE)$_2$(GGGS)$_2$(EAAAK)$_2$ is an effective linker.

Example 5

Autocleavage of Linker of CBP21-(EAAAR)$_3$-NCTU2-(his)$_6$ Under Various Buffer Solutions with Different pH Values

The steps of Examples 5-13 are the same as the steps of Example 3, and the only difference is that the fusion proteins containing various linkers and the cleavage buffer solutions with various pH values are used. Specifically, the purified fusion proteins of Examples 5-13 respectively contain various linkers (i.e., CBP21-primary amino acid sequence-NCTU2-(His)$_6$). When the linker undergoes cleavage, the fusion protein is divided into NCTU2-(His)$_6$ (36kD) and CBP21 (18kD), and the different molecular weights thereof can be clearly observed. Further, the cleavage buffer solutions with various pH values are respectively used in Examples 5-13 to find out a suitable pH range of the cleavage buffer solutions with each type of the linkers.

Figure 8A:
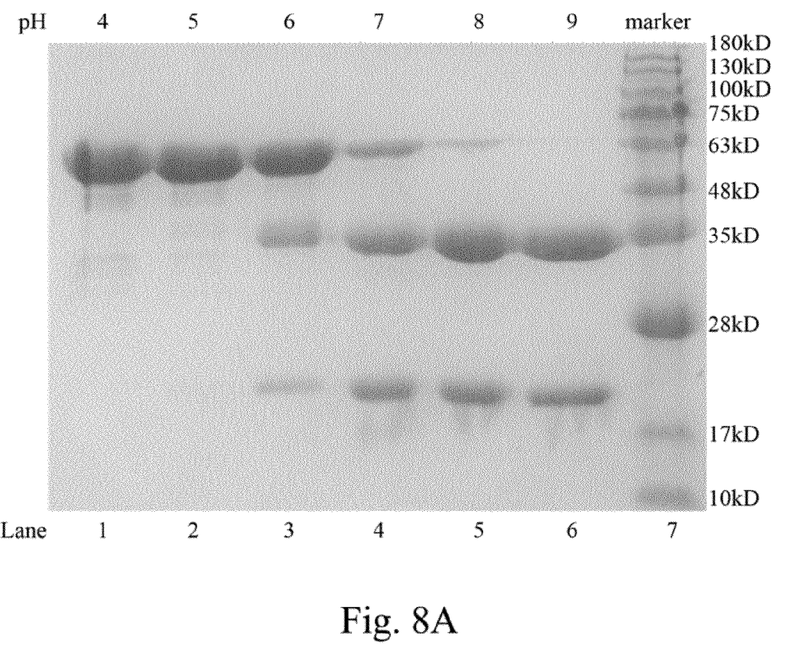
FIG. 8A is the SOS-PAGE analyses of autocleavage of linker of CBP21-$(EAAAR)_3$-NCTU2-$(His)_6$ under various cleavage buffer solutions with different pH values. Lane 1: pH=4; Lane 2: pH=5; Lane 3: pH=6; Lane 4: pH=7; Lane 5: pH=8; Lane 6: pH=9; Lane 7: marker.

In example 5, the fusion protein is CBP21-(EAAAR)$_3$-NCTU2-(His)$_6$. As shown in FIG. 8A, the linker undergoes cleavage under the buffer solutions with pH=6-9.

Example 6

Autocleavage of Linker of CBP21-(EGGGK)$_3$-NCTU2-(His)$_6$ Under Various Buffer Solutions with Different pH Values

Figure 8B:
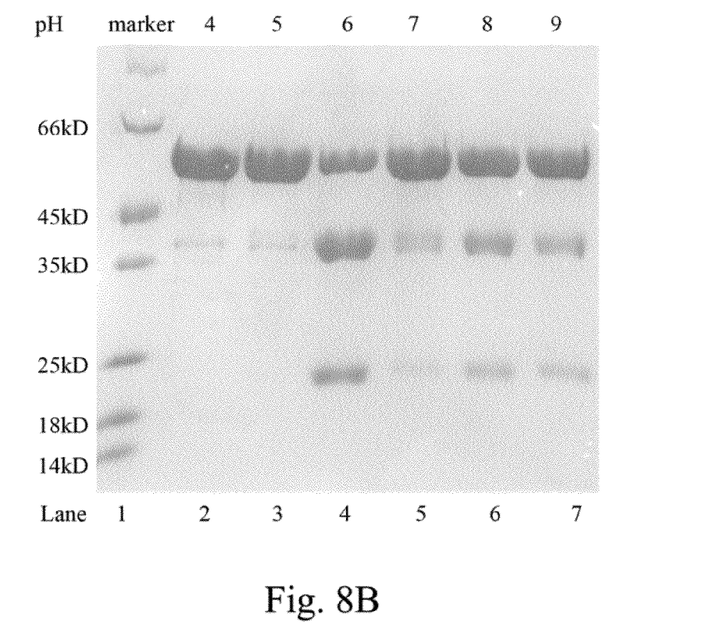
FIG. 8B is the SDS-PAGE analyses of autocleavage of linker of CBP21-$(EGGGK)_3$-NCTU2-$(His)_6$ under various cleavage buffer solutions with different pH values. Lane 1: marker; Lane 2: pH=4; Lane 3: pH=5; Lane 4: pH=6; Lane 5: pH=7; Lane 6: pH=8; Lane 7: pH=9.

In example 6, the fusion protein is CBP21-(EGGGR)$_3$-NCTU2-(His)$_6$. As shown in FIG. 8B, the linker undergoes cleavage under the buffer solutions with pH=6-8.

Example 7

Autocleavage of Linker of CBP21-(EGGGR)$_3$-NCTU2-(His)$_6$ Under Various Buffer Solutions with Different pH Value

Figure 8C:
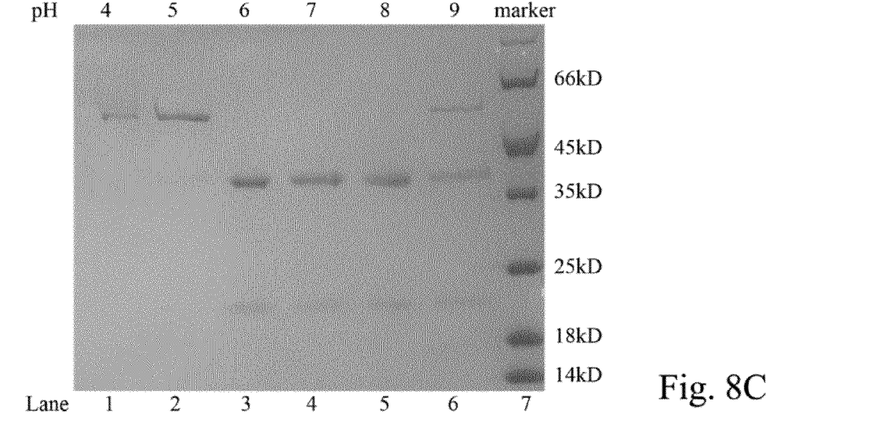
FIG. 8C is the SDS-PAGE analyses of autocleavage of linker of CBP21-$(EGGGR)_3$-NCTU2-$(His)_6$ under various cleavage buffer solutions with different pH values. Lane 1: pH=4; Lane 2: pH=5; Lane 3: pH=6; Lane 4: pH=7; Lane 5: pH=8; Lane 6: pH=9; Lane 7: marker.

In example 7, the fusion protein is CBP21-(EGGGR)$_3$-NCTU2-(His)$_6$. As shown in FIG. 8C, the linker undergoes cleavage under the buffer solutions with pH=6-8.

Example 8

Autocleavage of Linker of CBP21-(DAAAK)$_3$-NCTU2-(His)$_6$ Under Various Buffer Solutions with Different pH Values

Figure 8D:
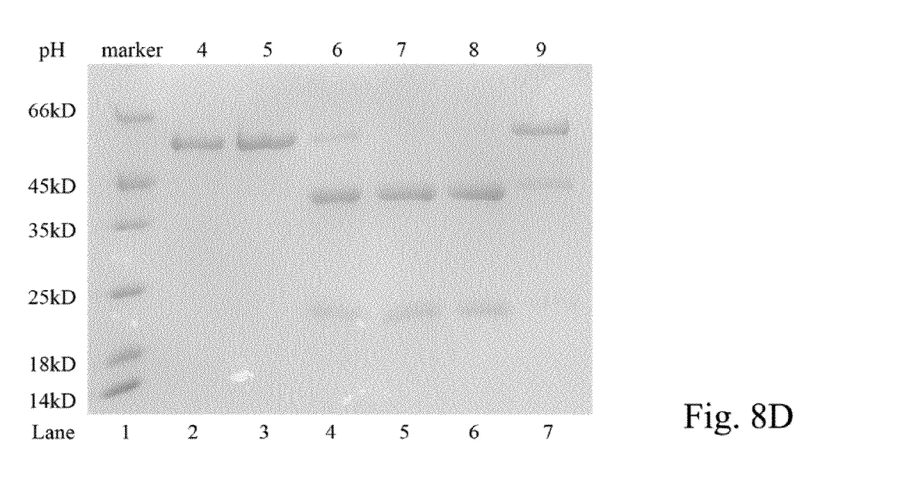
FIG. 8D is the SOS-PAGE analyses of autocleavage of linker of CBP21-$(DAAAK)_3$-NCTU2-$(His)_6$ under various cleavage buffer solutions with different pH values. Lane 1: marker; Lane 2: pH=4; Lane 3: pH=5; Lane 4: pH=6; Lane 5: pH=7; Lane 6: pH=8; Lane 7: pH=9.

In example 8, the fusion protein is CBP21-(DAAAK)$_3$-NCTU2-(His)$_6$. As shown in FIG. 8D, the linker undergoes cleavage under the buffer solutions with pH=6-8.

Example 9

Figure 8E:
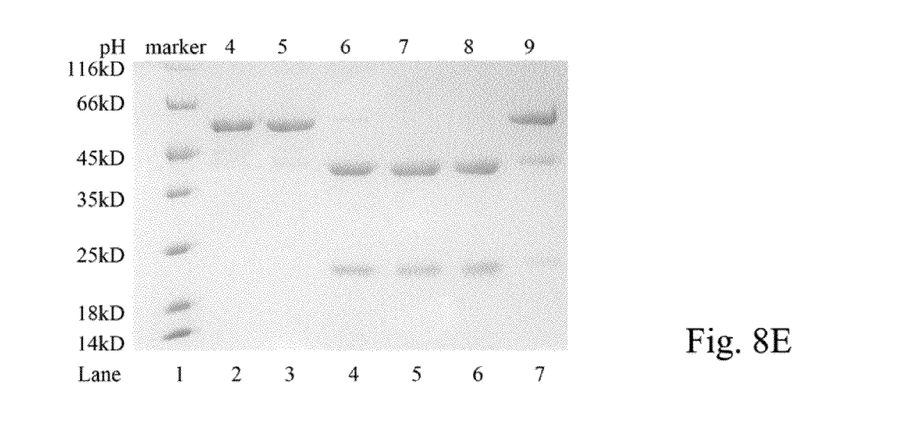
FIG. 8E is the SDS-PAGE analyses of autocleavage of linker of CBP21-(DAAAR)$_3$-NCTU2-(His)$_6$ under various cleavage buffer solutions with different pH values. Lane 1: marker; Lane 2: pH=4; Lane 3: pH=5; Lane 4: pH=6; Lane 5: pH=7; Lane 6: pH=8; Lane 7: pH=9.

Autocleavage of Linker of
CBP21-(DAAAR)$_3$-NCTU2-(His)$_6$ Under Various
Buffer Solutions with Different pH Values In example 9, the fusion protein is CBP21-(DAAAR)$_3$-NCTU2-(His)$_6$. As shown in FIG. 8E, the linker undergoes cleavage under the buffer solutions with pH=6-8.

Example 10

Figure 8F:
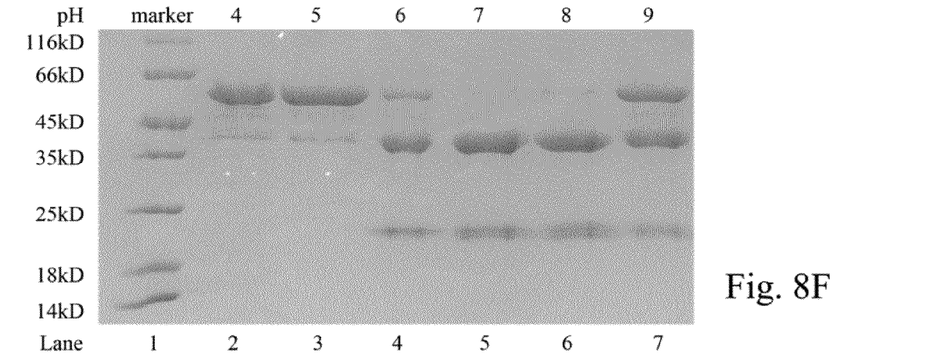
FIG. 8F is the SDS-PAGE analyses of autocleavage of linker of CBP21-(DGGGK)$_3$-NCTU2-(His)$_6$ under various cleavage buffer solutions with different pH values. Lane 1: marker; Lane 2: pH=4; Lane 3: pH=5; Lane 4: pH=6; Lane 5: pH=7; Lane 6: pH=8; Lane 7: pH=9.

Autocleavage of Linker of
CBP21-(DGGGK)3-NCTU2-(His)$_6$ Under Various
Buffer Solutions with Different pH Values In example 10, the fusion protein is CBP21-(DGGGK)$_3$-NCTU2-(His)$_6$. As shown in FIG. 8F, the linker undergoes cleavage under the buffer solutions with pH=6-8.

Example 11

Figure 8G:
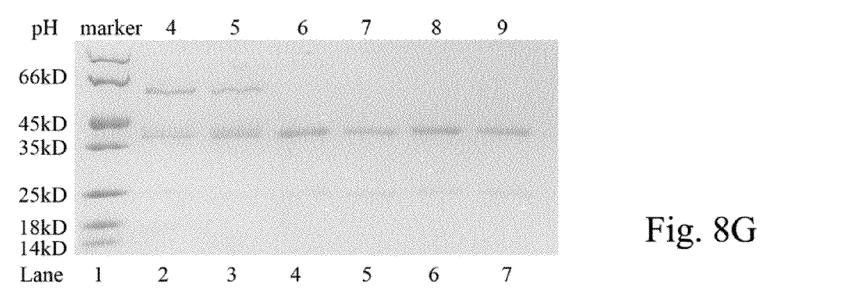
FIG. 8G is the SDS-PAGE analyses of autocleavage of linker of CBP21-(DGGGR)$_3$-NCTU2-(His)$_6$ under various cleavage buffer solutions with different pH values. Lane 1: marker; Lane 2: pH=4; Lane 3: pH=5; Lane 4: pH=6; Lane 5: pH=7; Lane 6: pH=8; Lane 7: pH=9.

Autocleavage of Linker of
CBP21-(DGGGR)$_3$-NCTU2-(His)$_6$ Under Various
Buffer Solutions with Different pH Values In example 11, the fusion protein is CBP21-(DGGGR)$_3$-NCTU2-(His)$_6$. As shown in FIG. 8G, the linker undergoes cleavage under the buffer solutions with pH=6-9.

Example 12

Figure 8H:
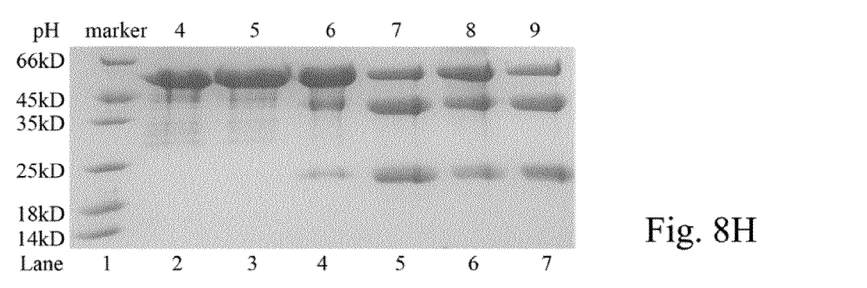
FIG. 8H is the SOS-PAGE analyses of autocleavage of linker of CBP21-(EAAK)$_3$-NCTU2-(His)$_6$ under various cleavage buffer solutions with different pH values. Lane 1: marker; Lane 2: pH=4; Lane 3: pH=5; Lane 4: pH=6; Lane 5: pH=7; Lane 6: pH=8; Lane 7: pH=9.

Autocleavage of Linker of
CBP21-(EAAK)$_3$-NCTU2-(His)$_6$ Under Various
Buffer Solutions with Different pH Values In example 12, the fusion protein is CBP21-(EAAK)$_3$-NCTU2-(His)$_6$. As shown in FIG. 8H, the linker undergoes cleavage under the buffer solutions with pH=6-9.

Example 13

Figure 8I:
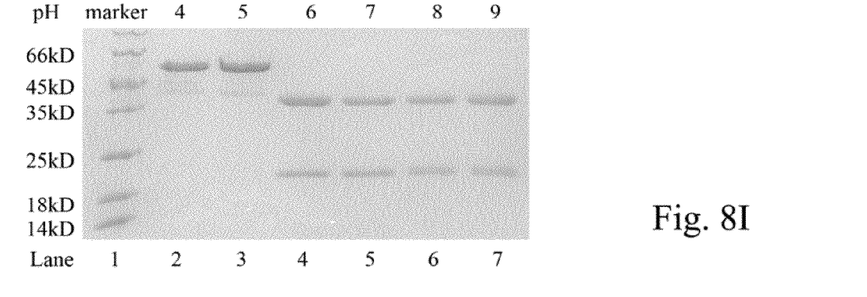
FIG. 8I is the SDS-PAGE analyses of autocleavage of linker of CBP21-(EAAAAK)$_3$-NCTU2-(His)$_6$ under various cleavage buffer solutions with different pH values. Lane 1: marker; Lane 2: pH=4; Lane 3: pH=5; Lane 4: pH=6; Lane 5: pH=7; Lane 6: pH=8; Lane 7: pH=9.

Autocleavage of Linker of
CBP21-(EAAAAK)$_3$-NCTU2-(His)$_6$ Under Various
Buffer Solutions with Different pH Values In example 13, the fusion protein is CBP21-(EAAAAK)$_3$-NCTU2-(His)$_6$. As shown in FIG. 8I, the linker undergoes cleavage under the buffer solutions with pH=6-9.

The primary amino acid sequence and the suitable pH range of the cleavage buffer solutions of Examples 5-13 are listed in Table 1.

TABLE 1

| | Primary amino acid sequence | Suitable pH range of cleavage buffer solution |
|---|---|---|
| Example 5 | (EAAAR)$_3$ (SEQ ID NO: 1) | 6-9 |
| Example 6 | (EGGGK)$_3$ (SEQ ID NO: 2) | 6-8 |
| Example 7 | (EGGGR)$_3$ (SEQ ID NO: 3) | 6-8 |
| Example 8 | (DAAAK)$_3$ (SEQ ID NO: 4) | 6-8 |
| Example 9 | (DAAAR)$_3$ (SEQ ID NO: 5) | 6-8 |
| Example 10 | (DGGGK)$_3$ (SEQ ID NO: 6) | 6-8 |
| Example 11 | (DGGGR)$_3$ (SEQ ID NO: 7) | 6-9 |
| Example 12 | (EAAK)$_3$ (SEQ ID NO: 8) | 6-9 |
| Example 13 | (EAAAAK)$_3$ (SEQ ID NO: 9) | 6-9 |

As shown in Table 1, suitable pH ranges of the cleavage buffer solutions are slightly different in accordance with various linkers.

Example 14

Autocleavage of Linker of
CBP21-(EAAAK)$_2$(KAAAE)$_2$-AF Under a Cleavage
Buffer Solution with pH=7

The steps of Example 14 are the same as the steps of Example 3, and the only difference is that the fusion protein is CBP21-(EAAAK)$_2$(KAAAE)$_2$-AF. It us noted that (EAAAK)$_2$(KAAAE)$_2$ refers to SEQ ID No:14.

Figure 9:
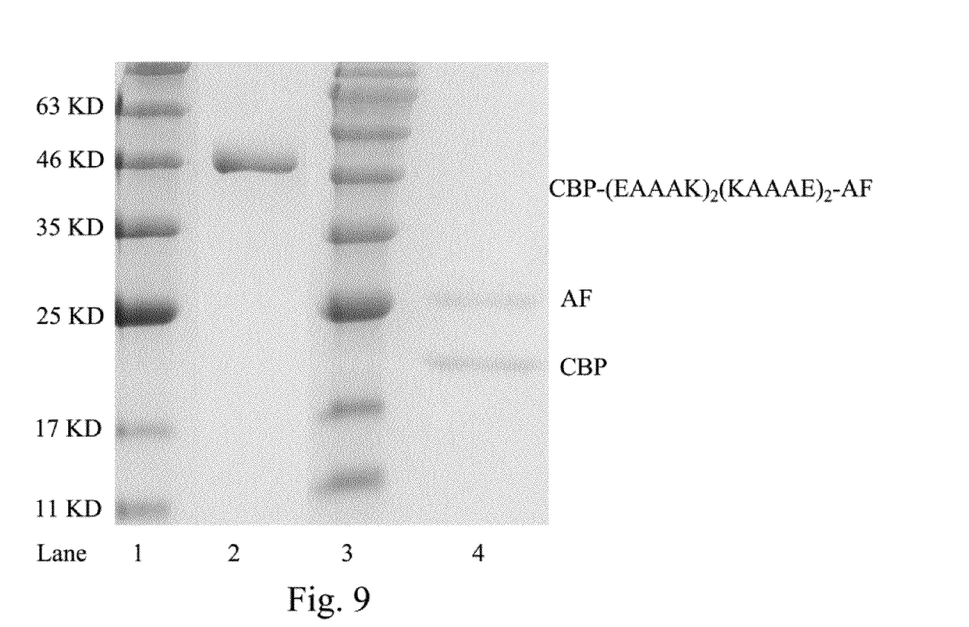
FIG. 9 is the SDS-PAGE analyses of autocleavage of linker of CBP21-(EAAAK)$_2$(KAAAE)$_2$-AF under a cleavage buffer solution with pH=7. Lane 1: marker; Lane 2: CBP21-(EAAAK)$_2$(KAAAE)$_2$-AF; Lane 3: marker; Lane 4: AF protein and CBP21.

As shown in FIG. 9 (Lane 4), the linker undergoes cleavage under the buffer solution with pH=7, and the AF protein and CBP are obtained.

Example 15

Autocleavage of Linker of CBP2-(KAAAE)$_4$-AF
Under a Cleavage Buffer Solution with pH=7

The steps of Example 15 are the same as the steps of Example 3, and the only difference is that the fusion protein is CBP21-(KAAAE)$_4$-AF. It is noted that (KAAAE)$_4$ refers to SEQ IS No:15.

Figure 10:
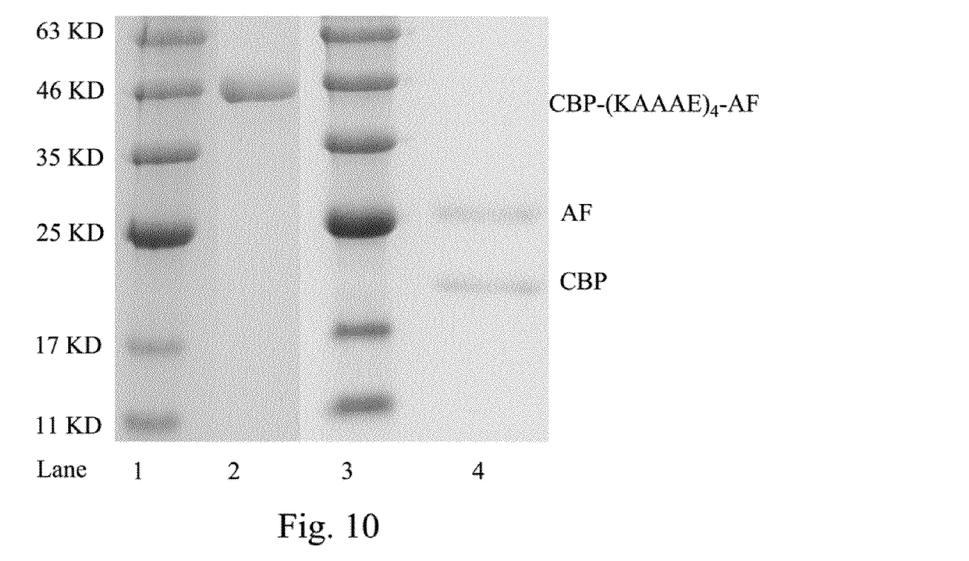
FIG. 10 is the SDS-PAGE analyses of autocleavage of linker of CBP21-(KAAAE)$_4$-AF under a cleavage buffer solution with pH=7. Lane 1: marker; Lane 2: CBP21-(KAAAE)$_4$-AF: Lane 3: marker; Lane 4: AF protein and CBP21.

As shown in FIG. 10 (Lane 4), the linker undergoes cleavage under the buffer solution with pH=7, and the AF protein and CBP are obtained.

Given above, the magnetic particles have the advantages of reusable, cheap, and able to simplify the process. Further, less material is required and the process is fast, such that the process can be applied to a large-scale protein purification process. The one-pot process can be performed to save much process time and increase convenience thereof. Compared to prior art, the process of the present disclosure does not use imidazole buffer solutions with various pH values to wash and use protease to break the linker, such that it is a fairly simple process. In addition, the target protein obtained by performing the process does not contain the tag and the linker. That is, the target protein can be free of non-native protein.

As mentioned above, the process can effectively solve the problem in the art and further provides a high cost-effective protein purification process to produce purified natural protein.

Although the present disclosure has been described in considerable detail with reference to certain embodiments thereof, other embodiments are possible. Therefore, the spirit and scope of the appended claims should not be limited to the description of the embodiments contained herein.

It will be apparent to those ordinarily skilled in the art that various modifications and variations may be made to the structure of the present disclosure without departing from the scope or spirit of the disclosure. In view of the foregoing, it is intended that the present disclosure cover modifications and variations thereof provided they fall within the scope of the following claims.

What is claimed is:

1. A method for producing a target protein, comprising steps of:
   (a) providing a crude extract including a fusion protein, the fusion protein comprising a tag, a target protein and a linker inserted between the tag and the target protein, wherein the linker has an amino acid sequence of SEQ ID NO:1;
   (b) binding magnetic particles and the fusion protein of the crude extract to form a magnetic particle-binding fusion protein; and
   (c) enabling autocleavage of the linker of the magnetic particle-binding fusion protein by using a cleavage buffer solution to release the target protein, wherein the cleavage buffer is TRIS buffer or phosphate buffer.

2. The method of claim 1, wherein the cleavage buffer solution has a pH value equal or greater than 6.

3. The method of claim 1, wherein the step (b) comprises binding the magnetic particles and the fusion protein of the crude extract in a solution.

4. The method of claim 3, further comprising a step of (b1) removing the solution to retain the magnetic particle-binding fusion protein after the step (b) and before the step (c).

5. The method of claim 4, further comprising a step of (b2) washing the magnetic particles after the step (b1) and before the step (c).

6. The method of claim 5, wherein the step (b2) comprises washing the magnetic particles by using a wash buffer solution, and the wash buffer solution has a pH value more than 7.

7. The method of claim 1, wherein the tag is a plurality of histidine.

8. The method of claim 1, wherein each of the magnetic particles has a surface with at least one group selected from the group consisting of a nickel ion, a cobalt ion, 1,6-diaminohexane, 1-oetylamine, oleylamine, tri-n-octylphosphine oxide, tri-n-octylphosphine and a combination thereof.

9. The method of claim 1, wherein the steps of the method are a one-pot process.

10. A one-pot process for producing a purified target protein, comprising steps of:
   (a) providing a crude extract including a fusion protein, the fusion protein comprising a tag, a target protein and a linker inserted between the tag and the target protein, wherein the linker has an amino acid sequence of SEQ ID NO: 1;
   (b) mixing the crude extract, a solution and magnetic particles to form a magnetic particle-binding fusion protein;
   (c) mixing a cleavage buffer solution and the magnetic particle-binding fusion protein to let the linker of the magnetic particle-binding fusion protein undergo autocleavage to thereby release the target protein and magnetic residues, wherein each of the magnetic residues includes the magnetic particle and the tag, and the cleavage buffer is TRIS butler or phosphate buffer; and
   (d) removing the target protein.

11. The process of claim 10, wherein the cleavage buffer solution has a pH value equal or greater than 6.

12. The process of claim 10, further comprising a step of (b1) removing the solution to retain the magnetic particle-binding fusion protein after the step (b) and before the step (c).

13. The process of claim 12, wherein the step of (b1) comprises removing the solution by fixing the magnetic particle-binding fusion protein by a magnet.

14. The process of claim 12, further comprising a step of (b2) washing the magnetic particles after the step (b1) and before the step (c).

15. The process of claim 14, wherein the step (b2) comprises washing the magnetic particles by using a wash buffer solution, and the wash buffer solution has a pH value more than 7.

16. The process of claim 10, wherein the step (d) comprises removing the target protein by fixing the magnetic particles with a magnet.

17. The process of claim 10, wherein the tag is a plurality of histidine.

18. The process of claim 10, wherein each of the magnetic particles has a surface with at least one group selected from the group consisting of a nickel ion, a cobalt ion, 1,6-diaminohexane, 1-octylamine, oleylamine, tri-n-octylphosphine oxide, tri-n-octylphosphine and a combination thereof.

* * * * *

SEQUENCE LISTING

<160> NUMBER OF SEQ ID NOS: 15

<210> SEQ ID NO 1
<211> LENGTH: 15
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 1

Glu Ala Ala Ala Arg Glu Ala Ala Ala Arg Glu Ala Ala Ala Arg
 1               5                  10                  15

<210> SEQ ID NO 2
<211> LENGTH: 15
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 2

Glu Gly Gly Gly Lys Glu Gly Gly Gly Lys Glu Gly Gly Gly Lys
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 3

Glu Gly Gly Gly Arg Glu Gly Gly Gly Arg Glu Gly Gly Gly Arg
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 4

Asp Ala Ala Ala Lys Asp Ala Ala Ala Lys Asp Ala Ala Ala Lys
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 5

Asp Ala Ala Ala Arg Asp Ala Ala Ala Arg Asp Ala Ala Ala Arg
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: The peptide sequence is used as a linker to connect a target protein and a tag

<400> SEQUENCE: 6

Asp Gly Gly Gly Lys Asp Gly Gly Gly Lys Asp Gly Gly Gly Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 7

Asp Gly Gly Gly Arg Asp Gly Gly Gly Arg Asp Gly Gly Gly Arg
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 8

Glu Ala Ala Lys Glu Ala Ala Lys Glu Ala Ala Lys
1               5                   10

<210> SEQ ID NO 9
<211> LENGTH: 18
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 9

Glu Ala Ala Ala Ala Lys Glu Ala Ala Ala Ala Lys Glu Ala Ala Ala
1               5                   10                  15

Ala Lys

<210> SEQ ID NO 10
<211> LENGTH: 15
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 10

Glu Ala Ala Ala Lys Glu Ala Ala Ala Lys Glu Ala Ala Ala Lys
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 11

Glu Ala Ala Ala Lys Glu Ala Ala Ala Lys
1               5                   10

```
<210> SEQ ID NO 12
<211> LENGTH: 20
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 12

Lys Ala Ala Ala Glu Lys Ala Ala Ala Glu Glu Ala Ala Ala Lys Glu
 1               5                  10                  15

Ala Ala Ala Lys
            20

<210> SEQ ID NO 13
<211> LENGTH: 28
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 13

Lys Ala Ala Ala Glu Lys Ala Ala Ala Glu Gly Gly Gly Ser Gly Gly
 1               5                  10                  15

Gly Ser Glu Ala Ala Ala Lys Glu Ala Ala Ala Lys
            20                  25

<210> SEQ ID NO 14
<211> LENGTH: 20
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 14

Glu Ala Ala Ala Lys Glu Ala Ala Ala Lys Lys Ala Ala Ala Glu Lys
 1               5                  10                  15

Ala Ala Ala Glu
            20

<210> SEQ ID NO 15
<211> LENGTH: 20
<212> TYPE: PRT
<213> ORGANISM: Artificial Sequence
<220> FEATURE:
<223> OTHER INFORMATION: The peptide sequence is used as a linker to
      connect a target protein and a tag

<400> SEQUENCE: 15

Lys Ala Ala Ala Glu Lys Ala Ala Ala Glu Lys Ala Ala Ala Glu Lys
 1               5                  10                  15

Ala Ala Ala Glu
            20
```